United States Patent [19]

Pinsl-Ober et al.

[11] Patent Number: 5,350,458
[45] Date of Patent: Sep. 27, 1994

[54] METHOD FOR CLEANING A DIAGNOSTIC ANALYZER

[75] Inventors: Judith Pinsl-Ober, Tutzing; Roland Schenk, Weilheim, both of Fed. Rep. of Germany

[73] Assignee: Boehringer Mannheim GmbH, Mannheim, Fed. Rep. of Germany

[21] Appl. No.: 19,826

[22] Filed: Feb. 19, 1993

Related U.S. Application Data

[60] Continuation of Ser. No. 825,354, Jan. 24, 1992, abandoned, which is a division of Ser. No. 580,442, Sep. 10, 1990, abandoned.

[30] Foreign Application Priority Data

Sep. 29, 1989 [DE] Fed. Rep. of Germany ....... 3932641

[51] Int. Cl.$^5$ .................. B01F 17/00; B01F 17/30; B08B 3/08; B08B 9/02
[52] U.S. Cl. .................. 134/22.1; 134/22.11; 134/22.12; 134/22.14; 134/26; 134/28; 252/95; 252/527; 252/354; 252/173; 252/528; 252/401
[58] Field of Search ............... 134/22.1, 22.11, 22.12, 134/22.14, 26, 28; 252/95, 527, 354, 173, 528, 401

[56] References Cited

U.S. PATENT DOCUMENTS

| | | | |
|---|---|---|---|
| 3,973,998 | 8/1976 | Datta et al. | 252/527 |
| 4,104,190 | 8/1978 | Hartshorn | 252/95 |
| 4,444,598 | 4/1984 | Sakagami | 134/22.12 |
| 5,077,008 | 12/1991 | Kralovic et al. | 252/95 |
| 5,178,830 | 1/1993 | Riera Aixalá | 134/22.1 |

*Primary Examiner*—Richard O. Dean
*Assistant Examiner*—Zeinab El-Arini
*Attorney, Agent, or Firm*—Nikaido Marmelstein Murray & Oram

[57] ABSTRACT

The invention provides a cleaning solution and a method of using the cleaning solution for cleaning diagnostic analyzers. The solution contains a rapidly wetting surfactant and an inorganic or organic acid. The invention provides rapid and effective cleaning of proteins from all types of materials used for components of automatic analyzers.

14 Claims, 1 Drawing Sheet

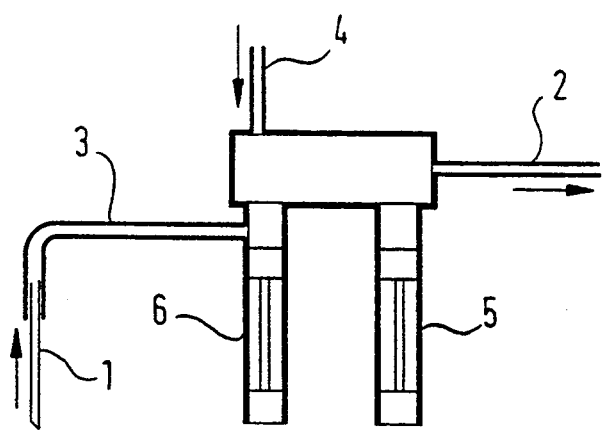

METHOD FOR CLEANING A DIAGNOSTIC ANALYZER

This application is a continuation of application Ser. No. 07/825,354 filed Jan. 24, 1992, now abandoned, which is, a Rule 1.60 division of application Ser. No. 07/580,442 filed Sep. 10, 1990, now abandoned.

FIELD OF THE INVENTION

The invention concerns a cleaning solution in particular for use in diagnostic analyzer systems for immunology and clinical chemistry.

In diagnostic analyzer systems for immunology and clinical chemistry, components of the system should be usable for a variety of different tests without subsequent tests being influenced by their "predecessors" i.e. without the so-called carry-over. If one wants to avoid the use of disposable equipment it is thus necessary to clean the "dirty" system components. In order to work rapidly and efficiently with automated analyzers the goal should be to achieve the maximum frequency of analyses which is possible on the instrument. The adherent dirt (in particular proteins) must therefore be completely removed within a short time. The cleaning should therefore be rapidly effective (if possible within a few seconds) and extend to a multitude of proteins (enzymes, antibodies, conjugates) which in turn can adsorb to a multitude of materials (plastics such as e.g. polymethyl methacrylate or Teflon, high-grade steel, glass etc.).

In this connection, typical problems are the problems of carry-over which occur with analyzer systems such as cuvette carry-over ((a) reagent to sample, (b) reagent to reagent, (c) sample to sample) or a probe carry-over (including tubes, syringes and valves; from (d) reagent to sample, (e) sample to sample, (f) reagent to reagent).

Automated diagnostic analyzers have been cleaned up to now using special cleaning procedures (cf e.g. DE-A-32 38 679; US-A-4 444 598; DD-C-3 238 679, DD-A-154 134 and US-A-4 248 642) or special cleaning solutions have been used for the individual components of the analyzer systems such as e.g. for electrodes (cf. JA-A-57 067 856 and JA-B-88 002 343).

SUMMARY OF THE INVENTION

The object of the present invention is therefore to provide a cleaning solution, especially for diagnostic analyzers which avoids the use of special cleaning procedures and which can be used for all components of the analyzer system, and with which the problems of carry-over can be solved simply and on a broad basis. The cleaning solutions should fulfil in particular the following criteria on a broad basis in automated diagnostic analyzers for clinical chemical tests or immunochemical tests:

cleaning within a few seconds;
removal of all sorts of contamination by proteins in cuvettes, pipetting probes and tubing systems with a single cleaning solution;
the cleaning action should be equally effective on the various materials which are used for the above-mentioned components of automated diagnostic analyzers e.g. glass, plastics, high-grade steel etc.;
the diagnostic tests should not be influenced by the cleaning solution; and
the cleaning agent should have an adequate bactericidal and fungicidal efficacy.

This object is achieved with the subject matter of the present invention according to claim 1.

BRIEF DESCRIPTION OF THE DRAWING

FIG. 1 is a diagram of an immunochemical analyzer. Element 1 is the probe, element 2 is the waste line, element 3 is teflon tubing, and element 4 is the inlet pipe.

DESCRIPTION OF THE PREFERRED EMBODIMENTS

The invention provides a cleaning solution, in particular for diagnostic analyzers, which is characterized in that it contains a rapidly wetting surfactant chosen from the group of sulphosuccinic acid esters, fluorosurfactants and secondary alkanesulphonates having a wetting time (according to the Draves test) of less than 20 seconds at a concentration of 0.3% by weight of the surfactant at 25° C., and an inorganic or organic acid with a $pK_s$ value of more than 2.5, and has a maximum pH value of 4.0.

A surfactant from the group of sulphosuccinic acid esters (as described e.g. in EP-A 0 071 410, 0 071 411 and 0 071 413) fluorosurfactants (as described e.g. in Seifen-Öle-Fette-Wachse 104 (1978) 429–432) and secondary alkanesulphonates (preferably with 12 to 18 carbon atoms) is used as the rapidly wetting surfactant. Two or more surfactants can also be used.

In this connection, those surfactants are preferably used which, apart from a wetting time of less than 20 seconds, in particular of less than or equal to 10 seconds, measured according to the Draves test (Draves wetting time; cf. Example 8) at a concentration of 0.3% by weight have an interfacial tension of <45 mN/m at the effective concentration in the cleaning solution.

Surfactants which are particularly preferred according to the present invention are sodium dihexyl sulphosuccinate (DHSS), sodium dioctyl sulphosuccinate (DOSS), tetraethylammonium perfluoro-octane sulphonate (TAPS) and sodium dodecyl-2-sulphonate.

The concentration of the surfactants in the cleaning solution is not particularly critical and can vary in a large range. It depends in particular on the type of surfactant used according to the present invention, but also on the type and concentration of the other components of the cleaning solution according to the present invention. The surfactant concentration is usually in the range from 0.01% by weight up to the concentration of the limit of solubility of the surfactant in the solution, in particular between 0.05 and 1.0% by weight, and preferably between 0.1 and 0.5% by weight. As a rule the effectiveness already reaches a maximum at concentrations of ca. 0.5% by weight or even below, so that higher concentrations which, although they result in the same effect, are not necessary and are pointless for economic and environmental reasons. The surfactants should be adequately soluble in water at an effective concentration, especially at a concentration which has a maximum effect, and they should be preferably effective in an acid range at pH values of <4. Acids of medium strength with a $pK_s$ value of >2.5, preferably organic acids, in particular from the group of mono, di- and tricarboxylic acids which are substituted if desired, are used as the acids. Substituted carboxylic acids are preferably hydrocycarboxylic acids. Preferred examples of acids used according to the present invention are citric acid, tartaric acid, succinic acid etc. but also e.g. formic acid, acetic acid etc. Two or more acids can also be used.

The concentrations of the acids in the cleaning solution according to the present invention can also vary in a wide range. The most suitable concentration depends in particular on the type of acids used, but also on the other components, especially the surfactant used. The acids are preferably at a concentration in the range from 0.001 mol/l to 0.5 mol/l cleaning solution, and in particular in the range from 0.01 to 0.1 mol/l cleaning solution.

Since the effectiveness of the cleaning solutions according to the present invention in general decreases with increasing pH, the pH value of the cleaning solution should not exceed a value of 4.

The production of the cleaning solutions according to the present invention can be carried out in a known manner by dissolving the constituents, whereby the surfactants and the acids can be dissolved simultaneously or successively. The surfactant is preferably dissolved as the first constituent. It can also be expedient to dissolve one or all constituents at a higher temperature. A completely desalted water, as is usually employed for such cleaning operations, is used when the cleaning solutions according to the present invention are applied in diagnostic analyzer systems.

The cleaning solutions according to the present invention are distinguished by a rapid and good cleaning action on a broad basis. They are effective for all components of a diagnostic analyzer system which come into contact with sample materials (serum, plasma etc.) and test reagents and are therefore eminently suitable for use as a cleaning solution for diagnostic analyzer systems in particular automated analyzers. The cleaning solutions according to the present invention have in particular the following desirable features in particular for an application in diagnostic analyzer systems:

the various components of an automated diagnostic analyzer can be cleaned with a single cleaning solution;

the cleaning is carried out within seconds;

the removal of contamination of various sorts containing protein, as occurs in automated analyzers in clinical chemistry and immunology is possible-and this contamination can be removed from the various materials which are used in automated diagnostic analyzers;

they can be washed out easily and thus the subsequent diagnostic tests are not influenced;

they have bactericidal and fungicidal action.

The following examples are intended to describe the invention in more detail without being limited by them. The details of percentages and amounts which are mentioned above or which follow refer to weight and details of temperature refer to the celsius scale.

The following abbreviations are used:
CA = citric acid
TA = tartaric acid.

EXAMPLE 1

Production of Cleaning Solutions

Cleaning solution 1 is produced from 0.2% sodium dihexyl sulphosuccinate (DHSS) (Draves wetting time at 25° C.: 10 seconds (cf. Example 8); interfacial tension: 42 mN/m) and 25 to 50 mmol/l citric acid ($pK_{s1} = 3.13$).

Cleaning solution 2 is produced from 0.2% by weight sodium dioctyl sulphosuccinate (DOSS) (Draves wetting time: <0.2 seconds at 25° C.; interfacial tension: 28 mN/m) and 25 to 50 mmol/l citric acid ($pK_{s1} = 3.13$).

Cleaning solution 3 is produced from 0.1% by weight tetraethylammonium perfluoro-octane sulphonate (TAPS) (Draves wetting time: <20 seconds at 25° C.; interfacial tension: 23 mN/m) and 25 to 50 mmol/l citric acid ($pK_{s1} = 3.13$).

Cleaning solution 4 is produced from 0.2% by weight DHSS and 25 to 50 mmol/l tartaric acid ($pK_{s1} = 3.11$).

EXAMPLE 2

The cleaning process is exemplified by an immunochemical analyzer system, a diagram of which is shown in FIG. 1. The following steps are employed:

a) The cleaning solution (2500 µl) is taken up by the high grade steel probe (which serves to take up the cleaning solution, sample and reagents) via the Teflon tube 3 and ejected into the waste line 2.

b) The process a) is repeated. The total duration of action is 20 seconds.

c) Rinse with distilled water (through the probe 1 and inlet pipe 4);

d) The process c) is repeated.

Purpose of the Cleaning

After pipetting reagents, e.g. containing peroxidase, the pipetting system (1, 3, 5) must be cleaned so efficiently that a reagent which detects peroxidase by colour formation (substrate) can be pipetted. Thus a prerequisite for this is that all surfaces of the system on which the above-mentioned reagents containing peroxidase could be adsorbed are cleaned virtually quantitatively in order to avoid a colour reaction in the pipetting system. The minimization of the increase in signal of the substrate in the tubing system after standing for 20 min is thus a measure for the quality of the cleaning process.

EXAMPLE 3

The application of a cleaning solution according to the present invention is described using an analyzer system as an example.

Procedure for Cleaning a) The cuvettes (made of polymethyl methacrylate, if not stated otherwise) are filled in 10 seconds with the solution which is to be tested for carry-over via a steel probe.

b) The cuvette filled in this way is incubated for 10 min at room temperature and afterwards aspirated within 10 seconds with a steel probe.

c) The cleaning solution is pipetted into the cuvette via another steel probe; duration of action ca. 10 seconds;

d) The cuvettes are completely aspirated and then filled with water (duration of action of water also ca. 10 seconds) three times in succession and finally aspirated completely.

e) The degree of carry-over is determined by means of a colour reaction which is specific for the substance which is carried over.

In order to make a comparison with the state of the art, water is used instead of the cleaning solution after c).

A solution of ca. 20000 U/l lipase in 150 mmol/l Tris/citrate buffer, pH 7.6 is used as the carry-over solution.

The following Tables 1-5 show the superior cleaning effect of a cleaning solution according to the present invention for the carry-over of lipase.

TABLE 1

Effective concentration range of a surfactant according to the present invention

| % surfactant[1] in solution | carry-over (U lipase/l) | | |
|---|---|---|---|
| | DHSS | DOSS | TAPS |
| 0.00 | 1200 | 1200 | 1200 |
| 0.10 | 190 | 300 | 200 |
| 0.20 | 0 | — | — |
| 0.50 | 0 | — | — |

[1] In each case in the presence of 25 mmol/l citric acid

The following Table 2 illustrates the synergistic cleaning effect which occurs as a result of the combination according to the present invention of surfactant and acid.

TABLE 2

| | Carry-over (U lipase/l) | |
|---|---|---|
| Acid content % | in 0.2% DHSS solution | in water |
| 0.0 CA/TA | 1190 | 2000 |
| 0.2 CA | 560 | — |
| 0.5 CA | 0 | 1200 |
| 1.0 CA | 0 | — |
| 0.5 TA | 0 | 1080 |

The following Table 3 shows the effectiveness of a cleaning solution according to the present invention (combination of surfactant and medium-strength acid) compared to a strong acid.

TABLE 3

| | Carry-over (U lipase/l) |
|---|---|
| Addition of (25 mmol/l) | in 0.2% DHSS solution |
| without acid | 1190 |
| HCl | 650 (reference value for strong inorganic acid) |
| CA | 0 |
| TA | 0 |
| formic acid | 0 |
| succinic acid | 0 |

Table 4 shows the dependency of the effectiveness of a cleaning solution according to the present invention on the pH of the solution (the cleaning solution of Example 1 was adjusted to the stated pH value with citric acid/citrate buffer).

TABLE 4

| Carry-over (U lipase/l) | | | | |
|---|---|---|---|---|
| pH 2.3 | pH 2.6 | pH 3.0 | pH 4.0 | pH 5.0 |
| 0 | 0 | 0 | 200 | 1620 |

Table 5 shows the dependency of the effectiveness of the cleaning solution according to the present invention on the duration of action in comparison with commercially available conventional cleaning solutions.

TABLE 5

| Duration of action of the solution (seconds) | Carry-over (U lipase/l) | | | | | |
|---|---|---|---|---|---|---|
| | cleaning solution 1,2,4 | cleaning solution 3 | water | CA 0.5% | cf.[1] 1.0% | cf[2] 2.0% |
| 10 | 0 | 200 | 2000 | 1200 | 1900 | 1060 |
| 20 | 0 | 600 | — | — | — | — |
| 600 | 0 | 0 | 400 | 210 | 200 | 100 |

[1] Extran ® AP43
[2] Hitergent ® (producer: Hitachi, Japan)

EXAMPLE 4

Carry-over into an Immunological Test

The carry-over of a conjugate of peroxidase and antibodies into an immunological test is examined as described in Example 2. However, the procedure differs from Example 3 in that one rinses twice with cleaning solution and twice with water.

Carry-over Solution

Conjugate of peroxidase and polyclonal antibodies against TSH (40 U peroxidase/l) in 15 mmol/l phosphate buffer pH 6.9.

The carry-over is examined using a colour test. For this, after cleaning and washing according to Example 2, substrate solution (1.6 mmol/l ABTS (2,2'-azino-di[3-ethylbenzthiazoline-sulphonic acid(6)]-diammonium salt), 95 mmol/l phosphate-citrate buffer, pH 4.4, 3.1 mmol/l sodium perborate) is added, incubated for 20 min and the absorbance is determined at 422 nm. The results are shown in Table 6.

Table 6 shows the effectiveness of cleaning solutions according to the present invention compared to commercially available and common cleaning solutions exemplified by the carry-over of peroxidase antibody conjugates.

TABLE 6

| cleaning agents | Absorbance [mA] |
|---|---|
| cleaning solution 1 | 0 |
| cleaning solution 2 | 0 |
| reference[3] | 215 |
| reference[4] | 198 |
| water | 283 |

[3] 3% Extran ® AP22
[4] 3% Extran ® MA01
(for [1] [3] and [4] cf. Römpps Chemie-Lexicon, 8th Edition, 1981, page 1230).

EXAMPLE 5

Cleaning Effect on Different Proteins

The carry-over of three different enzymes is examined as described in Example 3.

a) Lactate dehydrogenase-1-isoenzyme

31000 U/l lactate dehydrogenase-1-isoenzyme in 0.43 mol/l carbonate buffer, pH 10.0 is used as the carry-over solution. The pipetting and washing steps are carried out as described in Example 3. The determination of enzyme which is carried over is carried out as described in Z. Clin. Chem. U. Clin. Biochem. 8 (1970), 658 and 10 (1972) 182. In accordance with this a solution of 49 mmol/l phosphate buffer, pH 7.5, 0.17 ml NADH and 0.6 mmol/l pyruvate is added, the absorbance is measured at 385 nm and the enzyme activity is determined.

Lactate Dehydrogenase (LDH)

The determination of LDH is analogous to the determination of lactate dehydrogenase-1-isoenzyme.

Cholesterol Oxidase

A solution of 240 U/l cholesterol oxidase in 100 mmol/l Tris buffer, pH 7.7 is used as the carry-over solution. The determination is carried out as described in Clin. Chem. 29 (1983) 1075. The reagent for the determination of cholesterol which is necessary for this is used without the addition of cholesterol oxidase. If cholesterol oxidase is carried over then a colour is formed.

Composition of the Reagent 100 mmol/l Tris buffer, pH 7.7
50 mmol/l magnesium chloride
1 mmol/l 4-aminophenazone
10 mmol/l sodium cholate
6 mmol/l phenol
4 mmol/l 3,4-dichlorophenol
0.6% fatty alcohol polyethylene glycolether
0.4 U/ml cholesterol esterase
0.2 U/ml peroxidase Table 7 shows the effect of cleaning solutions according to the present invention compared to water on the removal of different sorts of contamination.

TABLE 7

| Carry-over of | Carry-over (U/l) | | |
|---|---|---|---|
| | cleaning solutions | | |
| | 1, 4 | 3 | water |
| lactate dehydrogenase-1-isoenzyme | 0 | 0 | 50 |
| lactate dehydrogenase | 0 | 0 | 500 |
| cholesterol oxidase | 0 | | 20 |

EXAMPLE 6

Carry-over of Lipase Using Vessels Made of Different Materials

Test procedure analogous to Example 3 and Example 2, respectively:

TABLE 8

| Material | Carry-over of lipase (U/l) | |
|---|---|---|
| | cleaning solution 1 | water |
| polymethyl methacrylate | 0 | 2000 |
| glass | 0 | 700 |
| high grade steel | 0 | 300 |
| polytetrafluoro ethylene | 0*) | 100*) |

*) U peroxidase/l

EXAMPLE 7

Draves Test

The Draves test is a method for determining the relative wetting power of surfactant solutions on a cotton tape. 1% by weight aqueous solutions of the detergents to be tested are prepared with deionised water at 25° C. at ±1° C. The solutions are subsequently diluted to 0.3% by weight.

A measuring cylinder is filled with 550 ml of the diluted surfactant solution. A hook weighing 1 g is fastened to a 40 g weight by means of a one inch long nylon thread. The hook is fastened 0.25 inches from the end of a 9 inch long cotton tape (Synthron). The weight with the attached tape is lowered into the measuring cylinder (the weight is immersed) until the end of the tape is just above the surface of the solution. Then the whole component is dropped. A stop watch is started when the weight touches the bottom and it is stopped when the tape sinks at a constant speed. The measured time interval is defined as the wetting time.

We claim:

1. A method for cleaning an immunological or clinical chemistry diagnostic analyzer of proteins or other biological materials comprising
   i) providing a diagnostic analyzer having a receptacle adapted to contain a liquid sample and requiring cleaning; and
   ii) contacting said receptacle with an aliquot of an aqueous cleaning solution consisting of a rapidly wetting surfactant and an inorganic or organic acid, for a time sufficient that, when the aqueous cleaning solution is removed, the proteins or biological materials are also removed.

2. A method of claim 1 wherein the time of contacting is 20 seconds.

3. The method of claim 1, further comprising emptying said receptacle and subsequently re-filling said receptacle with another aliquot of said aqueous cleaning solution.

4. The method of claim 1, further comprising emptying said receptacle and subsequently rinsing said receptacle with distilled water.

5. The method of claim 1, wherein said diagnostic analyzer is adapted for serial analysis of a plurality of samples, and said receptacle is cleaned between analysis of a first and a second sample.

6. The method of claim 1 wherein the surfactant of said aqueous cleaning solution is selected from the group consisting of sodium dihexyl sulfosuccinate (DHSS), sodium dioctyl sulfosuccinate (DOSS) and tetraethylammonium perfluoro-octane sulfonate (TAPS).

7. The method of claim 1 wherein the acid of said aqueous cleaning solution is an organic acid.

8. The method of claim 7 wherein the acid is chosen from the group of the mono-, di-, tricarboxylic acids and hydroxycarboxylic acids.

9. The method of claim 8 wherein the acid selected from the group consisting of citric acid, tartaric acid and succinic acid.

10. The method of claim 9 wherein the acid is present in an amount from 0.001 mol/l to 0.5 mol/l cleaning solution.

11. The method of claim 1 wherein the acid is present in an amount from 0.01 to 0.1 mol/l cleaning solution.

12. A method for cleaning a diagnostic analyzer comprising
   i) providing a diagnostic analyzer having a receptacle adapted to contain a liquid sample;
   ii) filing said receptacle with an aliquot of an aqueous cleaning solution consisting of a rapidly wetting surfactant chosen from the group consisting of sulfosuccinic acid ester, fluorosurfactants and secondary alkanesulfonates, said surfactant having a wetting time (according to the Draves Test) of less than 20 seconds at a concentration of 0.3% by weight at 25° C., said surfactant being present in an amount from 0.05 to 1.0% by weight of said cleaning solution and an amount of an inorganic or organic acid with a $pk_s$ value of more than 2.5 which is effective to impart a maximum pH value of 4.0 to said cleaning solution.

13. The method of claim 12 wherein the surfactant of said aqueous cleaning solution is present in an amount from 0.1 to 0.5% by weight.

14. A method for cleaning a diagnostic analyzer comprising
   i) providing a diagnostic analyzer having a receptacle adapted to contain a liquid sample;
   ii) filling said receptacle with an aliquot of an aqueous cleaning solution consisting of a rapidly wetting surfactant selected from the group consisting of sodium dihexyl sulfosuccinate (DHSS), sodium dioctyl sulfosuccinate (DOSS) and tetraethylammonium perfluorooctane sulfonate (TAPS), said surfactant being present in an amount from 0.05 to 1.0% by weight in relation to the cleaning solution, and an acid selected from the group consisting of citric acid, tartaric acid and succinic acid, said acid being present in an amount of from the minimum amount which is effective to impart a maximum pH value of 4.0 to said cleaning solution up to 0.5 mol/l of cleaning solution;
   iii) allowing said aqueous cleaning solution to contact surfaces of said receptacle for a sufficient amount of time to allow cleaning of said receptacle.

* * * * *